(12) United States Patent
Sekiya

(10) Patent No.: US 7,675,614 B2
(45) Date of Patent: Mar. 9, 2010

(54) WAFER INSPECTING METHOD AND DEVICE

(75) Inventor: Kazuma Sekiya, Ota-Ku (JP)

(73) Assignee: Disco Corporation, Tokyo (JP)

( * ) Notice: Subject to any disclaimer, the term of this patent is extended or adjusted under 35 U.S.C. 154(b) by 0 days.

(21) Appl. No.: 12/104,088

(22) Filed: Apr. 16, 2008

(65) Prior Publication Data

US 2008/0285021 A1 Nov. 20, 2008

(30) Foreign Application Priority Data

May 18, 2007 (JP) .............................. 2007-132781

(51) Int. Cl.
*G01N 21/00* (2006.01)
(52) U.S. Cl. .............. 356/237.4; 356/237.1; 356/237.6
(58) Field of Classification Search ... 356/237.1–237.6, 356/239.3, 239.7, 239.8
See application file for complete search history.

(56) References Cited

U.S. PATENT DOCUMENTS

| 5,917,588 | A * | 6/1999 | Addiego ................... 356/237.2 |
| 6,585,471 | B2 * | 7/2003 | Odajima et al. ............. 414/403 |
| 7,239,127 | B2 * | 7/2007 | Odan et al. ............... 324/158.1 |
| 2002/0028399 | A1 * | 3/2002 | Nakasuji et al. .......... 356/237.5 |

FOREIGN PATENT DOCUMENTS

JP         A 11-173993         7/1999

* cited by examiner

*Primary Examiner*—Gregory J Toatley, Jr.
*Assistant Examiner*—Iyabo S Alli
(74) *Attorney, Agent, or Firm*—Greer, Burns & Crain, Ltd.

(57) ABSTRACT

A wafer inspecting method including the steps of scanning the surface of a wafer along a street by using a line sensor having a plurality of elements arranged in a line, and determining a deposited condition of foreign matter on the surface of the wafer near electrodes formed on both sides of the street according to image information obtained by the above scanning step. By the use of the linear sensor, it is possible to efficiently determine whether or not the electrodes are good.

5 Claims, 4 Drawing Sheets

WAFER INSPECTING METHOD AND DEVICE

BACKGROUND OF THE INVENTION

1. Field of the Invention

The present invention relates to a method and device for inspecting a wafer for the deposition of foreign matter.

2. Description of the Related Art

A wafer is formed with a plurality of devices such as ICs and LSIs, and these devices are partitioned by a plurality of streets. The wafer is cut by dicing along these streets to obtain the individual devices. Each device is mounted on a lead frame or the like and next packaged to be used in various electronic equipment. The surface of each device is formed with a plurality of electrodes arranged along each street, so as to allow the electrical connection with the lead frame.

However, there is a possibility that foreign matter such as cutting dust and grinding dust may be deposited to the devices during the fabrication steps, causing a reduction in quality of the devices due to the deposited foreign matter. To cope with this possibility, there has been proposed a method of detecting the deposited foreign matter such as cutting dust (see Japanese Patent Laid-open No. 11-173993, for example).

However, the scale of integration in each device is increased to result in size reduction. With such size reduction, the space between the electrodes becomes as small as 50 to 10 µm, for example. Accordingly, there arises a problem such that foreign matter such as cutting dust may be deposited over the adjacent electrodes to cause a short circuit between these electrodes. Further, checking the wafer for deposited foreign matter by using a microscope or the like is inefficient to cause a reduction in productivity.

SUMMARY OF THE INVENTION

It is therefore an object of the present invention to provide a method and device for inspecting a wafer which can efficiently inspect the surface of the wafer for the deposition of foreign matter such as cutting dust near the electrodes.

In accordance with an aspect of the present invention, there is provided a wafer inspecting method for inspecting a wafer along streets, the wafer being formed with a plurality of devices partitioned by the streets, the wafer inspecting method including the steps of scanning the surface of the wafer along the streets by using a line sensor having a plurality of elements arranged in a line; and determining a deposited condition of foreign matter on the surface of the wafer near electrodes formed on both sides of the streets according to image information obtained by the scanning step.

In accordance with another aspect of the present invention, there is provided a wafer inspecting device including a chuck table for holding a wafer formed with a plurality of devices partitioned by streets; inspecting means for inspecting the surface of the wafer held on the chuck table; and alignment means for aligning an inspection area of the wafer to the inspecting means; the inspecting means including a line sensor having a plurality of elements arranged in a line, displaying means for displaying image information obtained by scanning the surface of the wafer along the streets by the use of the line sensor, and recording means for recording the image information. Preferably, the inspecting means further includes determining means for determining whether or not electrodes formed on both sides of the street are good according to the image information.

Preferably, the wafer inspecting device further includes chuck table driving means for moving the chuck table in an X direction as a scanning direction of the line sensor; indexing means for moving the inspecting means in a Y direction orthogonal to the X direction, the Y direction being the same as the transverse direction of the street; a cassette mounting table for mounting a cassette in which a plurality of wafers are stored; extracting means for extracting one of the wafers stored in the cassette; a temporary placement table on which the wafer extracted by the extracting means is temporarily placed; and carrying means for carrying the wafer temporarily placed on the temporary placement table to the chuck table.

According to the present invention, the electrodes formed on both sides of the street are scanned by using the line sensor to thereby efficiently determine whether or not the electrodes are good according to the deposited condition of foreign matter. Further, in the case that the inspection of the wafer is performed by using the inspecting means after dicing the wafer, the scanning speed of the wafer in the inspecting device may be set so as to match with the cutting speed in a dicing device. In this case, the inspection of the wafer can be performed in timing with the dicing of the wafer, thereby improving the productivity.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Figure 1:
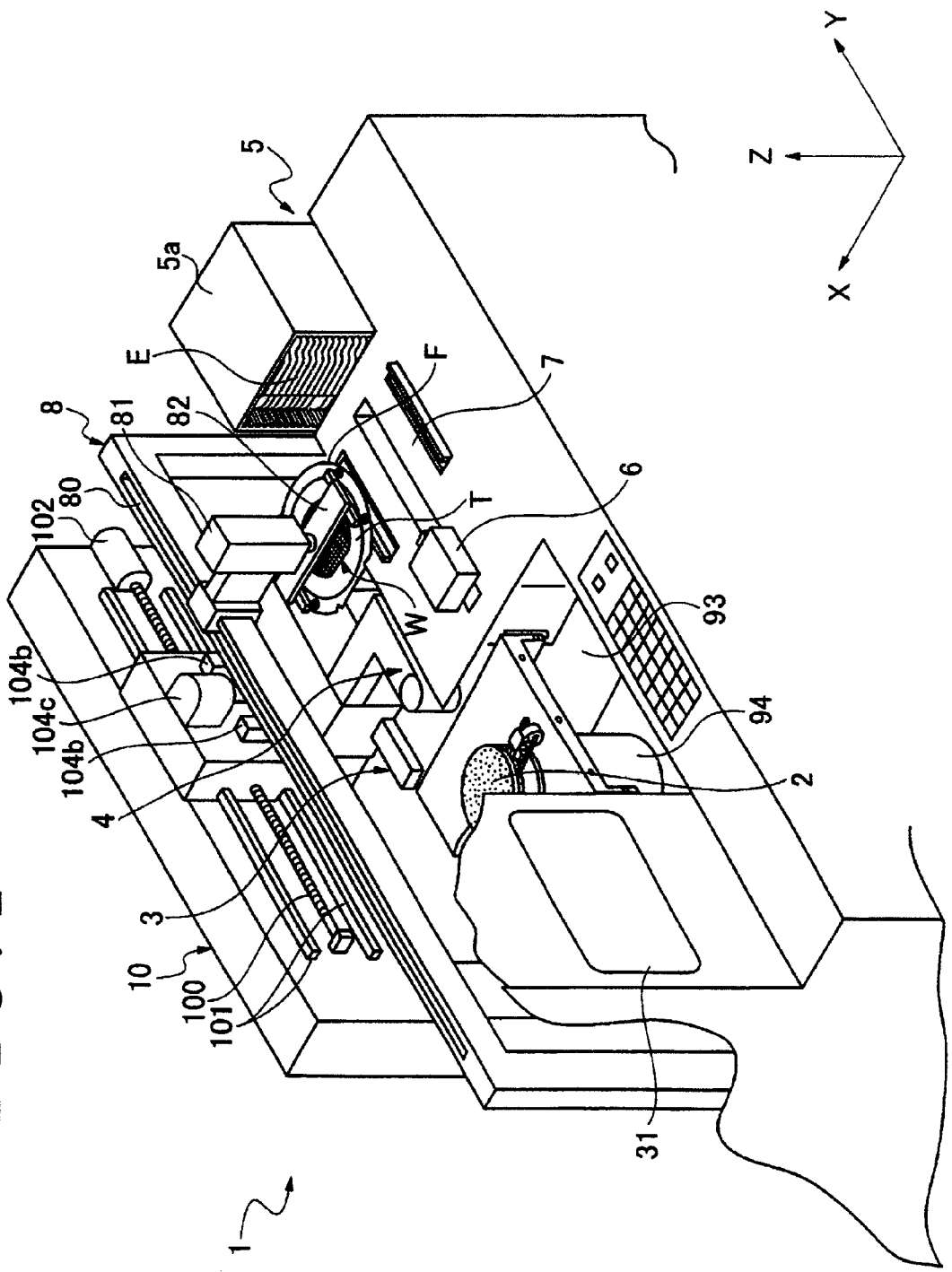
FIG. 1 is a perspective view of a wafer inspecting device according to a preferred embodiment of the present invention.
Figure 2:
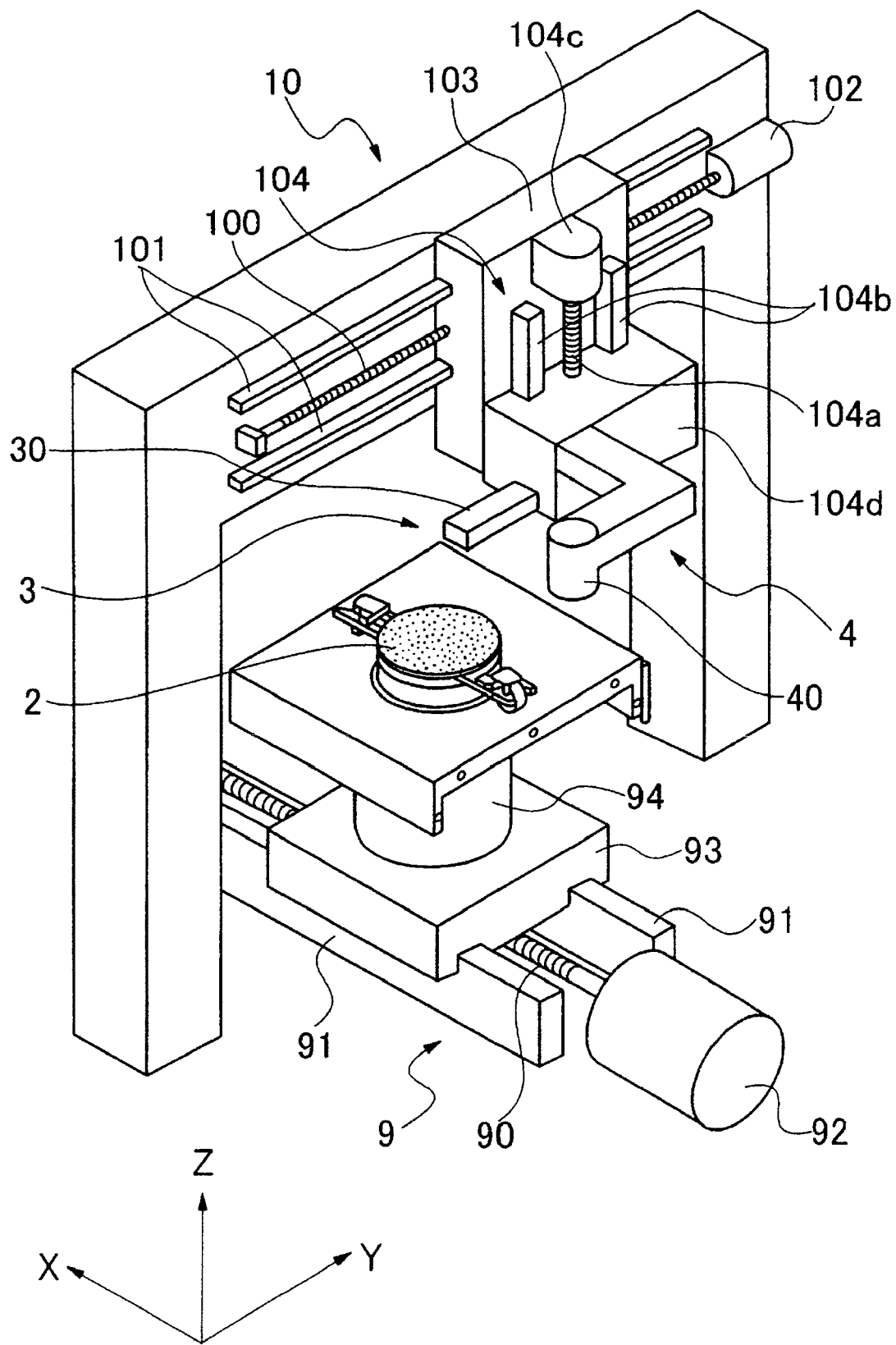
FIG. 2 is an enlarged perspective view of an essential part of the wafer inspecting device shown in FIG. 1.

Referring to FIG. 1, there is shown a wafer inspecting device 1 according to a preferred embodiment of the present invention. The wafer inspecting device 1 functions to detect foreign matter deposited to a wafer. The wafer inspecting device 1 includes a chuck table 2 for holding a wafer, inspecting means 3 for inspecting the surface of the wafer held on the chuck table 2 by using image information on the wafer, alignment means 4 for detecting an inspection area of the wafer and aligning this inspection area to the inspecting means 3, a cassette mounting table 5 for mounting a cassette 5a in which a plurality of wafers are stored, extracting means 6 for extracting one of the wafers stored in the cassette 5a, a temporary placement table 7 on which the wafer extracted by the extracting means 6 is temporarily placed, and carrying means 8 for carrying the wafer temporarily placed on the temporary placement table 7 to the chuck table 2. As shown in FIG. 2, the chuck table 2 is driven by chuck table driving means 9 to move in an X direction shown by an arrow X. The inspecting means 3 is driven by indexing means 10 to move in a Y direction shown by an arrow Y, the Y direction being orthogonal to the X direction.

As shown in FIG. 2, the chuck table driving means 9 includes a ball screw 90 extending in the X direction, a pair of guide rails 91 extending parallel to the ball screw 90, a motor 92 connected to one end of the ball screw 90 for rotating the ball screw 90, a slide plate 93 having an internal nut (not shown) threadedly engaged with the ball screw 90 and a lower portion slidably fitted with the guide rails 91, and a rotationally driving member 94 fixed to the upper surface of the slide plate 93 and having a pulse motor (not shown) for rotating the chuck table 2. Accordingly, when the motor 92 is driven to rotate the ball screw 90, the slide plate 93 is moved in the X direction as being guided by the guide rails 91, and the chuck table 2 is also moved in the X direction together with the slide plate 93.

As shown in FIG. 2, the indexing means 10 includes a ball screw 100 extending in the Y direction, a pair of guide rails 101 extending parallel to the ball screw 100, a pulse motor 102 connected to one end of the ball screw 100 for rotating the ball screw 100, a slide plate 103 having an internal nut (not shown) threadedly engaged with the ball screw 100 and a side portion slidably fitted with the guide rails 101, and vertically moving means 104 provided on the other side portion of the slide plate 103. Accordingly, when the pulse motor 102 is driven to rotate the ball screw 100, the slide plate 103 is moved in the Y direction as being guided by the guide rails 101, and the vertically moving means 104 is also moved in the Y direction together with the slide plate 103.

The vertically moving means 104 includes a ball screw 104a extending in a Z direction shown by an arrow Z as a vertical direction, a pair of guide rails 104b extending parallel to the ball screw 104a, a pulse motor 104c connected to one end of the ball screw 104a for rotating the ball screw 104a, and a vertically moving member 104d having an internal nut (not shown) threadedly engaged with the ball screw 104a and a side portion slidably fitted with the guide rails 104b. The alignment means 4 and the inspecting means 3 are fixed to the vertically moving member 104d.

Figure 3:
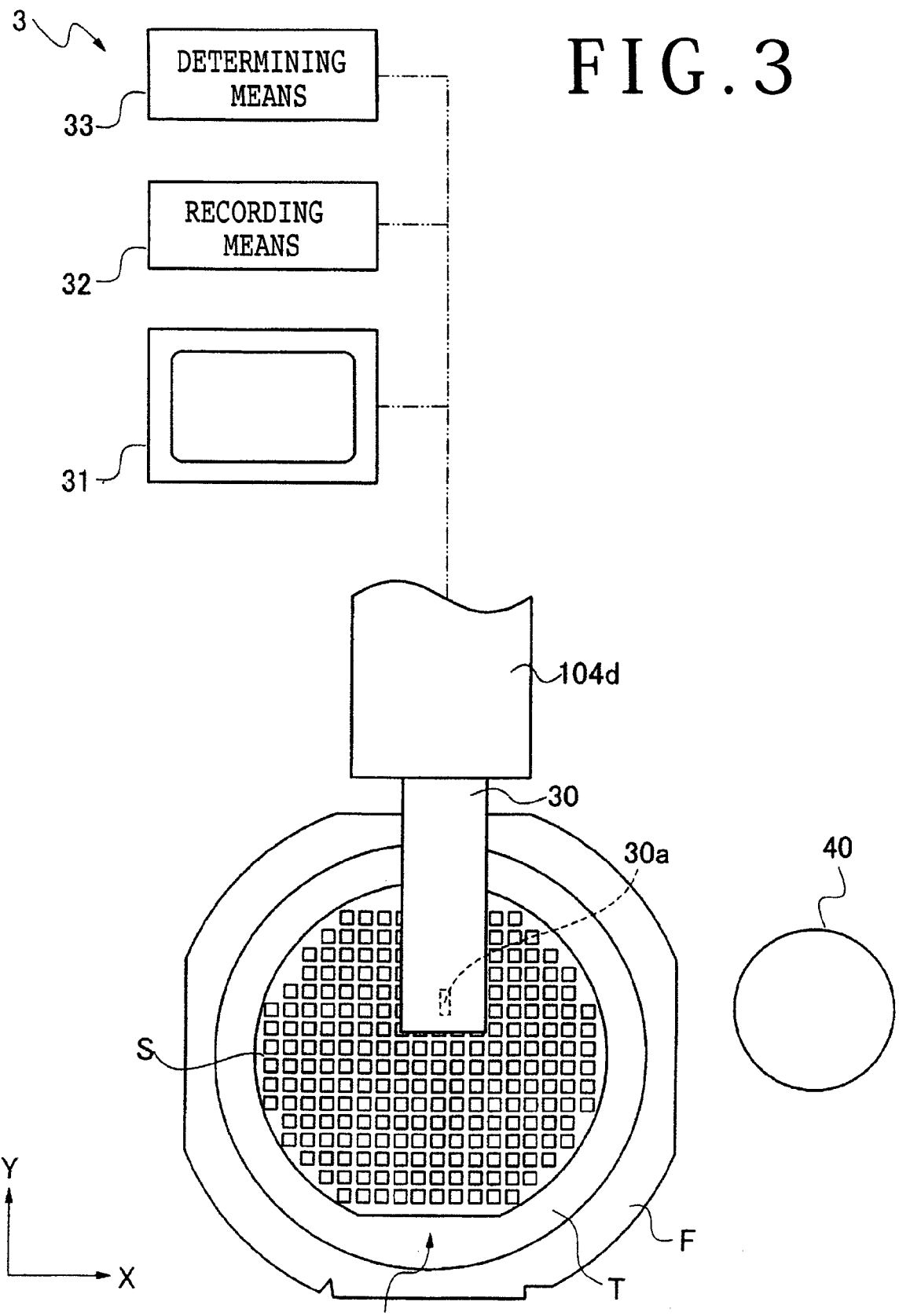
FIG. 3 is a schematic plan view showing the configuration of inspecting means.

The alignment means 4 has an imaging member 40 for imaging a wafer. The inspecting means 3 includes a line sensor 30 having an element array 30a (see FIG. 3) composed of a plurality of elements linearly arranged in the Y direction. As shown in FIG. 3, the element array 30a is positioned on an extension line extending from the imaging member 40 in the X direction. Each element is provided by a CCD having 5000 pixels arranged in series on a straight line having a length of 5 mm, for example.

As shown in FIG. 3, the inspecting means 3 further includes displaying means 31 for displaying image information obtained by the line sensor 30, recording means 32 for recording the image information obtained above, and determining means 33 for determining whether or not electrodes formed on the wafer are good (nondefective) according to the image information obtained above.

As shown in FIG. 1, the carrying means 8 includes a rail 80 extending in the Y direction, a moving member 81 adapted to move along the rail 80, and a suction member 82 for holding a ringlike frame F by suction. The suction member 82 is movable at least between the temporary placement table 7 and the chuck table 2. A wafer W as a subject to be inspected is integrated with the frame F through a tape T, and a plurality of such wafers W with the frames F are stored in the cassette 5a. The cassette mounting table 5 is vertically movable, so that the height of the wafer W to be extracted from the cassette 5a is adjusted by the vertical movement of the cassette mounting table 5. The frame F to be extracted is held by the extracting means 6 and then moved in the Y direction by the extracting means 6. When the wafer W is moved to the temporary placement table 7, the wafer W is removed from the extracting means 6 and then placed on the temporary placement table 7.

Thereafter, the suction member 82 is lowered to hold the frame F with the wafer W, and is next raised. In this raised condition of the wafer W, the moving member 81 is moved to carry the wafer W to a position directly above the chuck table 2. Thereafter, the suction member 82 is lowered to remove the wafer W and to set it on the chuck table 2. Thus, the wafer W integrated with the frame F is held on the chuck table 2. Thereafter, the chuck table 2 holding the wafer W is moved in the X direction to a position directly below the alignment means 4. In this position, the surface of the wafer W is imaged by the imaging member 40, and pattern matching is performed between the image obtained by the imaging member 40 and the image information preliminarily stored in a memory or the like, thereby detecting a street S extending in the X direction shown in FIG. 4, for example. Then, alignment is performed in the Y direction between the center of the street S along its width and the element array (photosensitive member) 30a of the line sensor 30.

Figure 4:
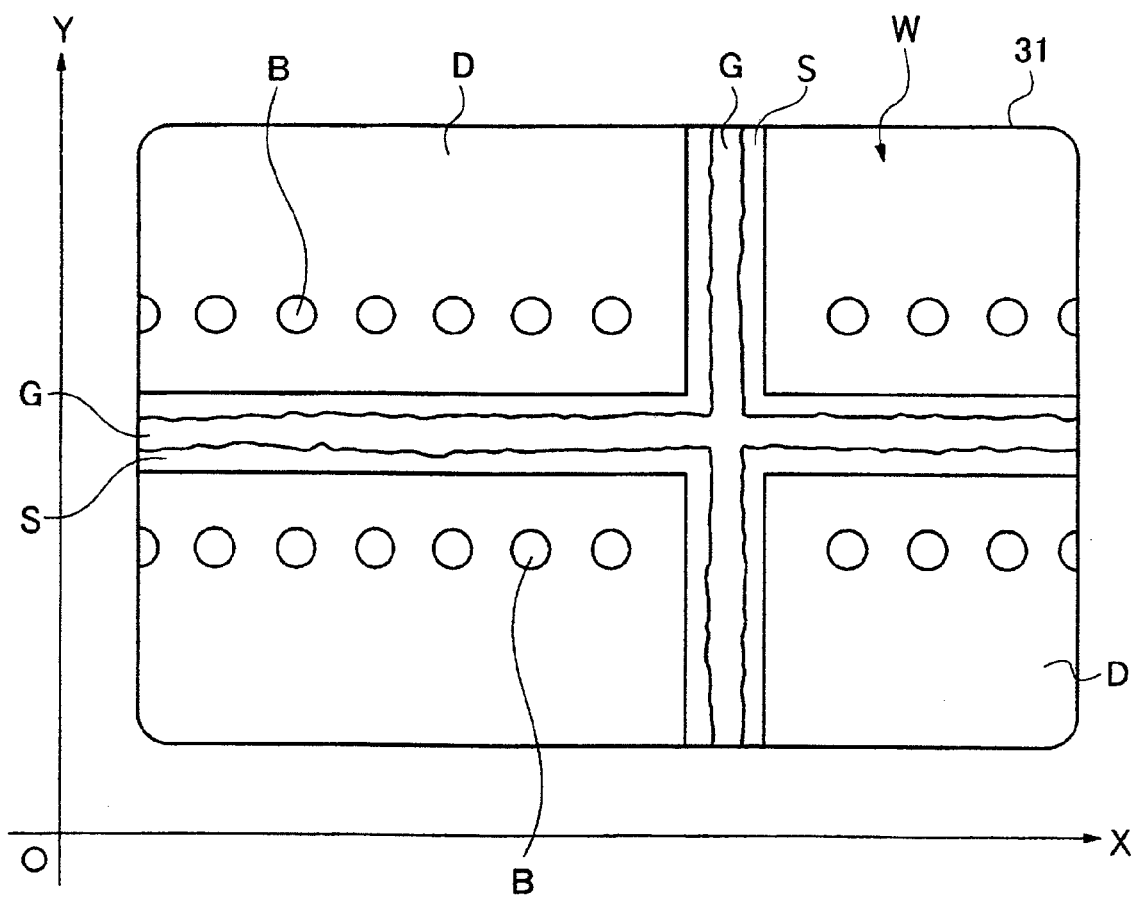
FIG. 4 is an enlarged view illustrating image information obtained by the inspecting means shown in FIG. 3.

As shown in FIG. 4, a plurality of crossing streets S extending in the X and Y directions are formed on the wafer W to partition a plurality of device areas D. In each device area D, a plurality of bonding pads B as a kind of electrodes are arranged in a line along each street S extending in the X direction. Further, each street S is previously cut to form a groove G. In inspecting the surface of the wafer W for deposited foreign matter, the chuck table 2 is moved in the X direction orthogonal to the direction of extension of the element array 30a, thereby scanning the surface of the wafer W along the subject street S extending in the X direction by using the line sensor 30 to obtain image information in the inspection area including the subject street S and the bonding pads B as the electrodes formed on both sides of this subject street S. In this scanning operation, the moving speed of the chuck table 2 is set to 50 mm/sec, for example.

The image information obtained by the line sensor 30 can be displayed by the displaying means 31. By viewing the displaying means 31, an operator can check whether or not foreign matter such as cutting dust is deposited on the surface of the wafer W, thereby preventing a short circuit between any adjacent ones of the plural bonding pads B as the electrodes. For example, in the case that the diameter of each bonding pad B is 5 μm, that the distance between the centers of any adjacent ones of the bonding pads B is 10 μm, and that foreign matter having a diameter of 5 to 10 μm is deposited over the adjacent bonding pads B, a short circuit occurs between these adjacent bonding pads B.

Further, the image information obtained by the line sensor 30 can be recorded by the recording means 32. The determining means 33 can binarize the image information obtained above, for example, thereby recognizing the shape and size of each bonding pad B. The deposition of foreign matter on any one of the bonding pads B may be determined by calculating the area of each bonding pad B from the number of pixels constituting the image information of each bonding pad B and by finding any bonding pad B having a larger area. This defective bonding pad B may be identified from the X and Y coordinates of the image information. In this manner, the deposition of foreign matter can be automatically determined by the determining means 33 without the need for visual checking on the displaying means 31 by the operator. In particular, since the line sensor 30 has a high resolution, accurate determination can be performed.

After finishing the inspection on both sides of the subject street S, the inspecting means 3 is indexed in the Y direction by the indexing means 10 to obtain image information on both sides of the next street S extending in the X direction and to perform similar inspection. This indexing operation is repeated to sequentially perform the inspection for all the streets S extending in the X direction. Thereafter, the chuck table 2 is rotated 90° to perform similar processing for all the other streets S. Thus, the inspection is performed over the entire surface of the wafer W.

In this preferred embodiment, the single line sensor 30 having the element array 30a composed of the plural elements linearly arranged is used to obtain image information on the electrodes arranged along a single street. As a modification, a plurality of such line sensors may be provided to simultaneously obtain image information on the electrodes arranged along a plurality of streets. In this case, image information can be efficiently obtained.

In the case that the inspection of the wafer is performed by using the inspecting device 1 after dicing the wafer, the scanning speed of the wafer in the inspecting device 1 may be set so as to match with the cutting speed in a dicing device. In this case, the inspection of the wafer can be performed in timing with the dicing of the wafer, thereby improving the productivity. For example, in the case of using a dicing device having such a configuration that a chuck table for holding the wafer is movable in the X direction and cutting means having a cutting blade is movable in the Y and Z directions, the chuck table in the dicing device and the chuck table in the inspecting device 1 may be adjusted in feed speed in such a manner that the time required for cutting of one street by the cutting blade (the time required for a travel of the chuck table) becomes equal to the time required for scanning of one street in the inspecting device 1.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A wafer inspecting method for inspecting a wafer along streets, said wafer being formed with a plurality of devices partitioned by said streets, said wafer inspecting method comprising the steps of:
    scanning the surface of said wafer along said streets by using a line sensor having a plurality of elements arranged in a line;
    determining a deposited condition of foreign matter on the surface of said wafer near or on electrodes formed on both sides of said streets according to image information obtained by said scanning step; and
    binarizing the image information to recognize a size and shape of each electrode to determine whether foreign matter is deposited on each electrode, and wherein a scanning speed of said wafer along said streets matches a cutting speed of said wafer.

2. A wafer inspecting device comprising:
    a chuck table for holding a wafer formed with a plurality of devices partitioned by streets; inspecting means for inspecting the surface of said wafer held on said chuck table; and alignment means for aligning an inspection area of said wafer to said inspecting means; said inspecting means including a line sensor having a plurality of elements arranged in a line, displaying means for displaying image information obtained by scanning the surface of said wafer along said streets by the use of said line sensor, said image information being binarized to recognize a size and shape of each electrode to determine whether foreign matter is deposited on each electrode and recording means for recording said image information, wherein said inspecting means further comprises means for calculating an area of each element from a number of pixels constituting said displayed image information of each element, and a scanning speed of scanning said surface of said wafer matches a cutting speed of said wafer.

3. The wafer inspecting device according to claim 2, wherein said inspecting means further includes determining means for determining whether or not electrodes formed on both sides of said streets are good according to said image information.

4. The wafer inspecting device according to claim 2, further comprising:
    chuck table driving means for moving said chuck table in an X direction as a scanning direction of said line sensor;
    indexing means for moving said inspecting means in a Y direction orthogonal to said X direction, said Y direction being the same as the transverse direction of said streets;
    a cassette mounting table for mounting a cassette in which a plurality of wafers are stored;
    extracting means for extracting one of said wafers stored in said cassette;
    a temporary placement table on which said wafer extracted by said extracting means is temporarily placed; and
    carrying means for carrying said wafer temporarily placed on said temporary placement table to said chuck table.

5. The wafer inspecting method of claim 1, further comprising the step of calculating an area of each element based on a number of pixels constituting said image information for each element.

* * * * *